(12) United States Patent
Schaller et al.

(10) Patent No.: US 9,827,141 B2
(45) Date of Patent: Nov. 28, 2017

(54) SYSTEMS AND TECHNIQUES FOR TISSUE MANIPULATION DURING OCULAR SURGERY

(71) Applicant: Novartis AG, Basel (CH)

(72) Inventors: Philipp Schaller, Stein am Rhein (CH); Reto Grueebler, Greifensee (CH)

(73) Assignee: Novartis AG (CH)

( * ) Notice: Subject to any disclaimer, the term of this patent is extended or adjusted under 35 U.S.C. 154(b) by 244 days.

(21) Appl. No.: 14/201,136

(22) Filed: Mar. 7, 2014

(65) Prior Publication Data

US 2014/0379024 A1    Dec. 25, 2014

Related U.S. Application Data

(60) Provisional application No. 61/837,977, filed on Jun. 21, 2013.

(51) Int. Cl.
| | |
|---|---|
| *A61F 9/007* | (2006.01) |
| *A61B 17/29* | (2006.01) |
| *A61B 17/30* | (2006.01) |

(52) U.S. Cl.
CPC .......... *A61F 9/00727* (2013.01); *A61B 17/29* (2013.01); *A61B 17/2909* (2013.01);
(Continued)

(58) Field of Classification Search
CPC .............. A61F 9/00709; A61F 9/00727; A61F 9/00736; A61B 17/29; A61B 17/30;
(Continued)

(56) References Cited

U.S. PATENT DOCUMENTS

| | | | | |
|---|---|---|---|---|
| 2,165,374 A | * | 7/1939 | Heilig ................ | A61B 17/30 606/133 |
| 4,955,887 A | * | 9/1990 | Zirm ................. | A61B 17/29 606/107 |

(Continued)

FOREIGN PATENT DOCUMENTS

| | | |
|---|---|---|
| DE | 29515489 | 12/1995 |
| JP | 2004216494 A2 | 8/2004 |

(Continued)

OTHER PUBLICATIONS

International Search Report for PCT/EP2014/054906, Publication No. WO2014/202243, dated Jun. 2, 2014, 4 pages.
(Continued)

*Primary Examiner* — Tuan V Nguyen
*Assistant Examiner* — Christian Knauss

(57) ABSTRACT

Tissue manipulation during ocular surgery may be achieved by a variety of systems and techniques. In particular implementations, a system may include spaced apart levers, hinge members, a grasping mechanism, and a guide mechanism located between the levers. A first hinge member may extend from one of the levers to the guide mechanism and move the guide mechanism in one of a proximal or distal direction when the levers are moved toward each other. The grasping mechanism may be coupled to the guide mechanism and extend distally from the guide mechanism. A second hinge member may extend from one of the levers and be coupled to a tube that surrounds a portion of the grasping mechanism. The second hinge member distally displaces the tube when the levers are moved towards each other. The relative motion of the guide mechanism and the tube may cause actuation of the grasping mechanism.

18 Claims, 4 Drawing Sheets

(52) U.S. Cl.
CPC .......... *A61B 17/30* (2013.01); *A61F 9/00709* (2013.01); *A61F 9/00736* (2013.01); *A61B 2017/292* (2013.01); *A61B 2017/2919* (2013.01); *A61B 2017/305* (2013.01)

(58) Field of Classification Search
CPC .... A61B 2017/2908; A61B 2017/2932; A61B 2017/301; A61B 2017/303; A61B 2017/305
See application file for complete search history.

(56) References Cited

U.S. PATENT DOCUMENTS

| | | | |
|---|---|---|---|
| 5,147,378 | A | 9/1992 | Markham |
| 5,540,530 | A | 7/1996 | Fazekas |
| 5,741,270 | A | 4/1998 | Hansen et al. |
| 5,752,960 | A | 5/1998 | Nallakrishnan |
| 5,893,877 | A | 4/1999 | Gampp et al. |
| 6,089,130 | A | 7/2000 | Wu |
| 6,306,155 | B1 | 10/2001 | Chandler et al. |
| 6,322,578 | B1 | 11/2001 | Houle et al. |
| 6,488,695 | B1 | 12/2002 | Hickingbotham |
| 6,730,076 | B2 | 5/2004 | Hickingbotham |
| D504,176 | S | 4/2005 | Vijfvinkel |
| 8,235,978 | B2 | 8/2012 | Ben Nun |
| 8,806,720 | B2 | 8/2014 | Wang |
| 2001/0056286 | A1 | 12/2001 | Etter et al. |
| 2002/0161398 | A1* | 10/2002 | Hickingbotham . A61B 17/2909 606/206 |
| 2005/0154375 | A1 | 7/2005 | McGowan et al. |
| 2006/0036270 | A1 | 2/2006 | Terao |
| 2009/0012519 | A1 | 1/2009 | Manrique et al. |
| 2010/0168787 | A1 | 7/2010 | Surti |
| 2011/0093068 | A1 | 4/2011 | Werblin |
| 2012/0116435 | A1* | 5/2012 | Nallakrishnan ........ A61B 17/29 606/174 |
| 2012/0245414 | A1 | 9/2012 | Verbeek |
| 2012/0318110 | A1 | 12/2012 | Lavelle et al. |
| 2013/0035671 | A1 | 2/2013 | Brand et al. |
| 2014/0135820 | A1 | 5/2014 | Schaller et al. |

FOREIGN PATENT DOCUMENTS

| | | |
|---|---|---|
| JP | 2008093241 A2 | 4/2008 |
| NL | 1014885 C2 | 10/2001 |
| WO | 2009061194 A1 | 5/2009 |
| WO | 2010064670 A1 | 6/2010 |

OTHER PUBLICATIONS

International Search Report and Written Opinion of the International Searching Authority, International Application No. PCT/2013/66575, dated Jan. 16, 2014, 9 pages.

* cited by examiner

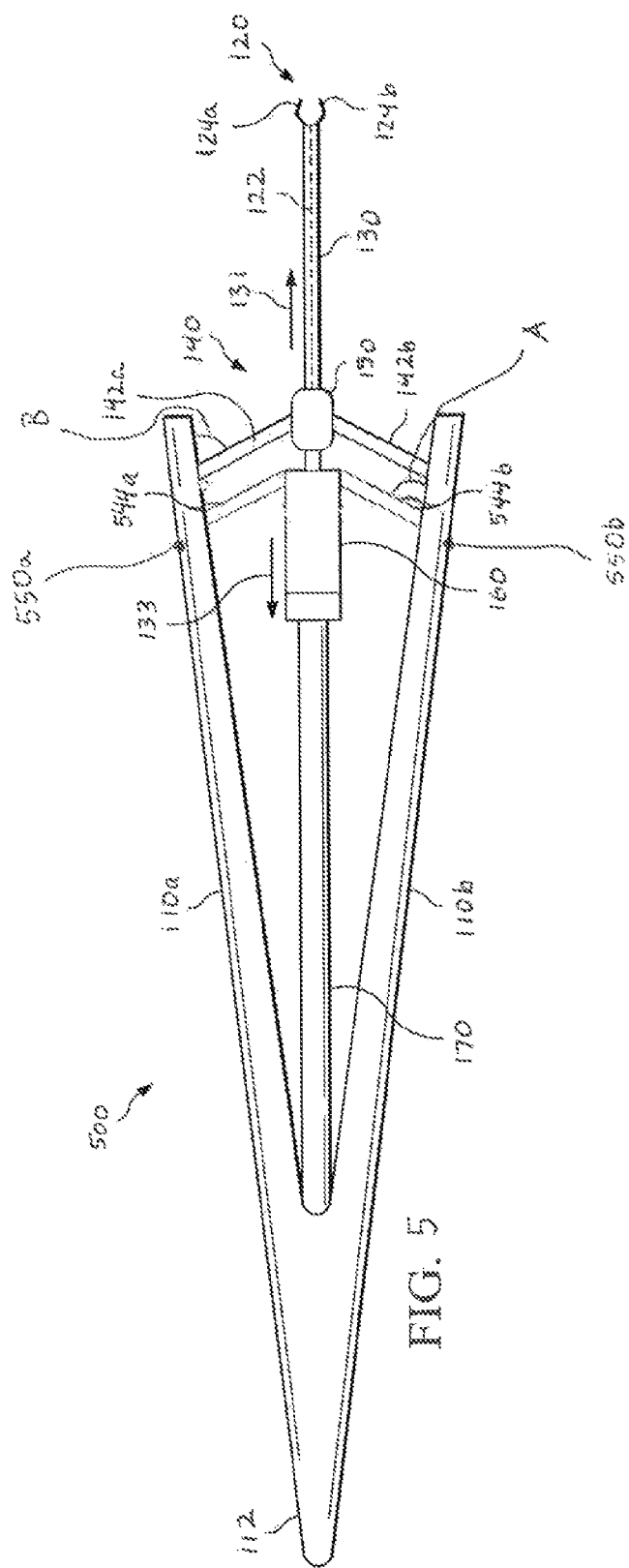

SYSTEMS AND TECHNIQUES FOR TISSUE MANIPULATION DURING OCULAR SURGERY

CROSS-REFERENCE TO RELATED APPLICATIONS

This application claims the benefit of U.S. Provisional Application No. 61/837,977 filed Jun. 21, 2013, the contents of which being incorporated herein by reference.

TECHNICAL FIELD

The present disclosure relates to ocular surgery and, more specifically, to tissue manipulation during ocular surgery.

BACKGROUND OF THE INVENTION

Trauma, age, or disease may cause the retina to peel away from its support tissue, a condition often termed retinal detachment. Retinal detachment is more common among those with severe myopia, but may also occur as a result of physical trauma to the eye, cataract surgery, or diabetic retinopathy. Initial detachments may be localized, but without rapid treatment, the entire retina may detach, leading to vision loss and blindness.

During some types of vitreoretinal surgery, portions of the retina must be removed. For example, during membranectomy, layers of unhealthy tissue may be removed from the retina with tiny instruments such as forceps, picks, and micro-dissection, involving separation of tissue layers with fluid jets.

SUMMARY

Various systems and techniques for manipulating tissue during ocular surgery are disclosed. In certain implementations, a system for tissue manipulation during ocular surgery may include levers, hinge members, a grasping mechanism, a tube, and a guide mechanism. The levers may be coupled together at one end and spaced apart from each other at another end. A first hinge member may extend from one of the levers to the guide mechanism, which is located between the levers, and be adapted to move the guide mechanism in one of a proximal or distal direction when the levers are moved toward each other. The grasping mechanism may be coupled to the guide mechanism and extend from distally therefrom. A second hinge member may extend from one of the levers and be coupled to a tube that surrounds a portion of the grasping mechanism. The second hinge member may be adapted to move the tube distally when the levers are moved towards each other. The second hinge member may, for example, be coupled to a hub that surrounds and is coupled to the tube. The motion of the guide mechanism relative to the tube may cause the grasping mechanism and the tube to move relative to each other and actuate the grasping mechanism. The tube may have a curved or straight configuration.

Some implementations may include a third hinge member and a fourth hinge member. The third hinge member may extend to the guide mechanism from the lever opposite the lever from which the first hinge member extends and be adapted to move the guide mechanism in one of a proximal or distal direction when the levers are moved toward each other. The fourth hinge member may be coupled to the tube and extend from the lever opposite the lever from which the second hinge member extends and be adapted to move the tube distally when the levers are moved toward each other.

In particular implementations, the hinge members may be adapted to bend when the levers are moved towards each other. For example, the hinge members may be adapted to form a curved shape when bent. In some implementations, the hinge members may be bent when the levers are in a non-activated state and then straighten when the levers are activated.

In certain implementations, a member may extend between the levers. The guide mechanism may be adapted to slideably receive the member. In some implementations, the guide mechanism may also slideably receive the tube.

The grasping mechanism may include a guide that runs through the tube and actuatable grasping arms at the distal end of the guide. The grasping arms may be adapted to move towards each other when engaged by a distal end of the tube.

Various other features will be apparent to those skilled in the art from the following description and the accompanying figures.

BRIEF DESCRIPTION OF THE DRAWINGS

FIG. 5 shows a side view of another example system for tissue manipulation.

DETAILED DESCRIPTION

While the example systems and methods disclosed herein may be described in the context of ocular surgical procedures, it is understood that such a context is merely exemplary. The example systems and methods may be applicable to numerous other applications and fields. Consequently, the scope of the disclosure is not intended to be limited to the ophthalmic arts but, rather, is applicable to any field or application where, for example, manipulation of small or delicate structures is required or desired.

Figure 1:
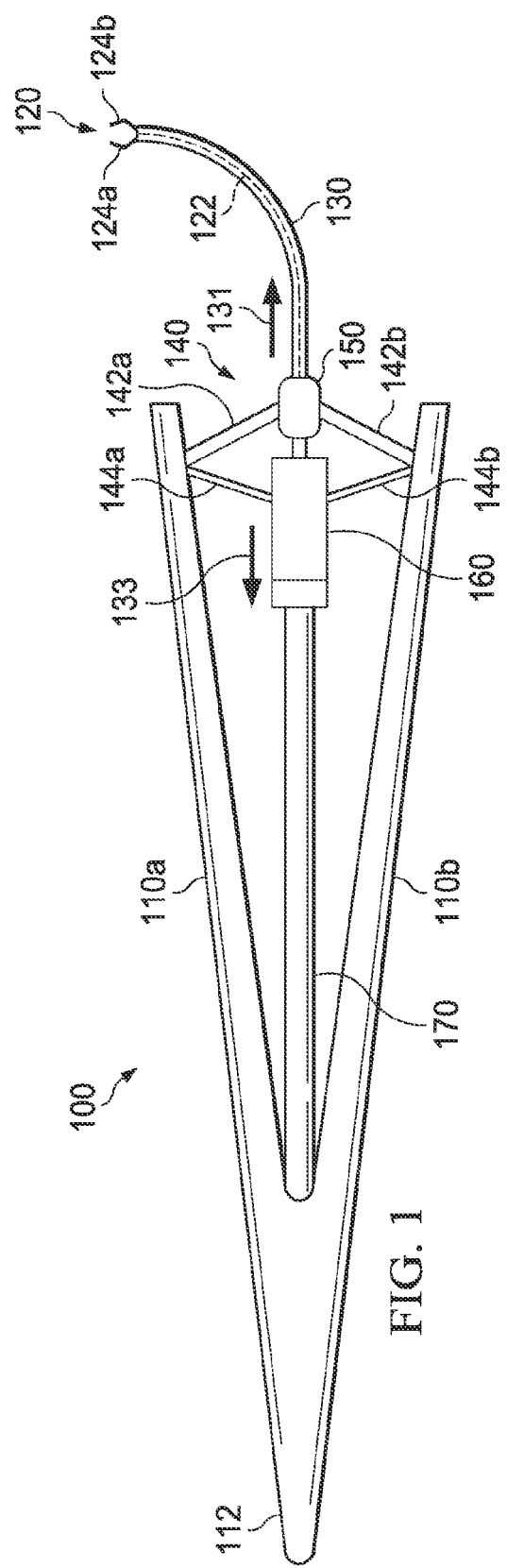
FIG. 1 shows a side view of an example system for tissue manipulation during ocular surgery.
Figure 2:
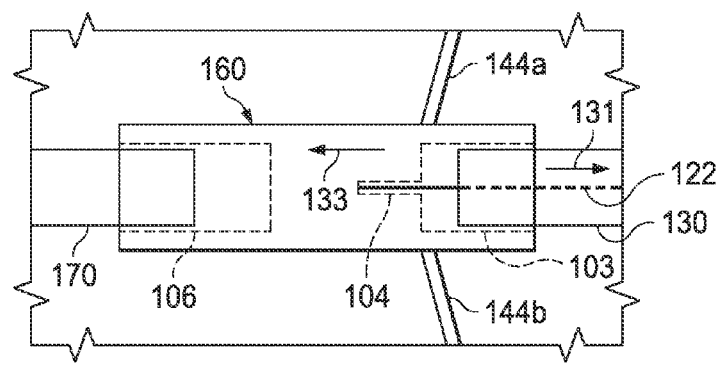
FIG. 2 shows a side view of an example guide mechanism for an ocular tissue manipulation system.

FIGS. 1 and 2 illustrate an example system 100 for tissue manipulation during ocular surgery. System 100 includes a pair of levers 110*a*, 110*b*, a grasping mechanism 120, and a tube 130. In operation, manipulation of levers 110 toward each other causes tube 130 to extend in the direction of arrow 131 and activate grasping mechanism 120. System 100 may be sized for removing particles from an eye during ocular surgery (e.g., vitreoretinal surgery).

Levers 110*a*, 110*b* are generally elongated and are coupled to each other at an end 112 in a manner to allow movement of the levers toward each other (e.g., in a pinching-like manner). Levers 110*a*, 110*b* may, for example, be integral, pinned, fused, or otherwise coupled to each other at end 112. Levers 110*a*, 110*b* may be made of stainless steel, titanium, plastic, or any other appropriate material.

In the illustrated implementation, a user may manipulate levers 110*a*, 110*b* by grasping them between thumb and fingers and moving them towards each other (e.g., in a pinching-like motion). In certain implementations, levers 110*a*, 110*b* may be part of a larger device, and the user may manipulate other portion of the device (e.g., handles) to manipulate levers 110*a*, 110*b*.

Grasping mechanism 120 includes a guide 122 that extends from between levers 110a, 110b and two or more grasping arms 124a, 124b coupled to the distal end of guide 122. Guide 122 links grasping arms 124 to the actuation of levers 110a, 110b. In some instances, a proximal end of the guide 122 may be received into a channel 104 formed in a guide mechanism 160 and fixedly secured thereto. Guide 122 may, for example, be coupled to guide mechanism 160 by adhesive, ultrasonic welding, force closure, or any other appropriate technique. Guide 122 may, for example, be a metal wire or a plastic filament, with round, oval, rectangular, or other desired cross-section. In particular implementations, guide 122 may have sufficient flexibility to conform a curved shape of the guide 122 during actuation of system 100. Grasping arms 124a, 124b may be coupled together at the distal end of guide 122 in a manner to allow movement of the grasping arms 124a, 124b towards each other (e.g., in a pinching-like manner). For example, grasping arms 124a, 124b may be pinned or fused to the distal end of guide 122. The guide 122 may be secured to the hub 160. Grasping mechanism 120 may be made of stainless steel, titanium, plastic, or any other appropriate material.

Tube 130 surrounds guide 122 of grasping mechanism 120 and extends from the hub 150 between levers 110a, 110b to grasping arms 124a, 124b. Tube 130 may have a circular, oval, rectangular, or other cross-section and be made of metal, plastic, or any other appropriate material. In some implementations, tube 130 may have sufficient rigidity to maintain the curved shape during actuation of system 100.

System 100 also includes a hinge assembly 140, a guide mechanism 160, and a member 170. These components cooperate with each other to extend tube 130 over and relative to guide 122 of grasping mechanism 120 when levers 110a, 110b are manipulated.

In the illustrated implementation, hinge assembly 140 includes two front hinge members 142a, 142b and two rear hinge members 144a, 144b. Front hinge members 142a, 142b are respectively coupled to levers 110a, 110b and also coupled to hub 150, which is coupled to tube 130. Front hinge members 142a, 142b may be coupled to levers 110a, 110b and/or hub 150 by being integral to, pinned to, fused to, or otherwise coupled to the components. In some implementations, the coupling may allow rotation of the front hinge members 142a, 142b at the coupling location. For example, the hinge members 142a, 142b may be coupled to the levers 110a, 110b, respectively, with a pinned connection. Thus, in such an example, the hinge members 142a, 142b are permitted to pivot relative to the levers 110a, 110b. In other implementations, the hinge members 142a, 142b may be coupled to the levers 110a, 110b such that the hinge members 142a, 142b are not permitted to freely pivot relative thereto. For example, the levers 110a, 110b and hinge members 142a, 142b may be integrally formed together. Thus, in some implementations, during actuation of the instrument 100, while some pivoting of the hinge members 142a, 142b may occur, the hinge members 142a, 142b primarily bend as a result of actuation of the instrument 100. In still other implementations, coupling of the hinge members 142a, 142b may not allow rotation at the coupling location relative to the levers 110a, 110b. Hub 150 may be integral with, fused to, adhered to, or otherwise coupled to tube 130.

Rear hinge members 144a, 144b are respectively coupled to levers 110a, 110b and to guide mechanism 160. Rear hinges 144 may be coupled to levers 110 and/or guide mechanism 160 by being integral to, pinned to, fused to, or otherwise coupled to the components. In some implementations, the coupling may allow rotation of the rear hinge members 144a, 144b at the coupling location. For example, the hinge members 144a, 144b may be coupled to the levers 110a, 110b, respectively, with a pinned connection. Thus, in such an example, the hinge members 144a, 144b are permitted to pivot relative to the levers 110a, 110b. In other, implementations, the hinge members 144a, 144b may be coupled to the levers 110a, 110b such that the hinge members 144a, 144b are not permitted to freely pivot relative thereto. For example, the levers 110a, 110b and hinge members 144a, 144b may be integrally formed together. Therefore, in some implementations, during actuation of the instrument 100, while some pivoting of the hinge members 144a, 144b may occur, the hinge members 144a, 144b primarily bend as a result of actuation of the instrument 100. In still other implementations, coupling of the hinge members 144a, 144b may not allow rotation at the coupling location relative to the levers 110a, 110b.

Guide mechanism 160 receives and is coupled to guide 122 of grasping mechanism 120. For example, the guide 122 may be received and secured into channel 104 to couple the guide 122 and guide mechanism 160. Guide mechanism 160 is also coupled to member 170, which extends between levers 110a, 110b. The member 170 may be slideably disposed in a channel 106 formed in the guide mechanism 160. Consequently, the member 170 and guide mechanism 160 are moveable relative to each other with the member 170 slideable within and guided axially along the channel 106. Guide 122 is coupled to guide mechanism 160 so that the guide 122 moves axially therewith. A proximal end of tube 130 may be slideably received into a channel 103 formed in the guide mechanism 160.

In certain modes of operation, system 100 is operated by a user (e.g., physician or other medical professional) grasping levers 110a, 110b and positioning grasping arms 124a, 124b in proximity (e.g., around) a tissue to be grasped. Once the grasping arms are in proximity to the tissue to be grasped, the user manipulates levers 110a, 110b toward each other. A change in distance between the levers 110a, 110b during actuation of the instrument 100 is referred to as "actuation displacement." The motion of levers 110 toward each other causes ends of the front hinge members 142 coupled to the hub 150 to move (e.g., by swinging, bending, straightening, or otherwise) toward grasping arms 124 in the direction of arrow 131. The movement of front hinge members 142a, 142b causes hub 150 to also move toward grasping arms 124. Because hub 150 is coupled to tube 130, the movement of hub 150 causes tube 130 to also move toward grasping arms 124. Thus, during actuation of the grasping levers 110a, 110b, the tube 130 is moved in the direction of arrow 131 within the channel 103. Simultaneously, the tube 130 is moved in the direction of arrow 131 so as to engage the grasping members 124a, 124b. As the tube 130 continues to move in the direction of arrow 131, the grasping members 124a, 124b are moved towards each other. An amount of movement of the grasping members 124a, 124b relative to a location on the instrument 100 that is stationary during actuation of the instrument 100, e.g., a point along member 170, such as the distal end of the member 170 may be termed "tip displacement."

At about the same time that front hinge members 142a, 142b are moving toward grasping arms 124a, 124b, ends of the rear hinge members 144a, 144b coupled to the guide mechanism 160 are moving away from grasping arms 124a, 124b in the direction of arrow 133 (e.g., by swinging, bending, straightening, or otherwise). Thus, the movement of rear hinge members 144a, 144b causes guide mechanism 160 to move in the direction of arrow 133 towards end 112. Because guide 122 is coupled to guide mechanism 160, the movement of guide mechanism 160 in the direction of arrow 133 also causes guide 122 to move in the direction of arrow 133 towards end 112. Moreover, because guide mechanism 160 slideably receives member 170 within channel 106, guide mechanism 160 moves along member 170 towards end 112. Thus, the cooperation between channel 106 and member 170 guides the guide mechanism 160 as it moves in the direction of arrow 133. As a result, a ratio of actuation displacement and tip displacement can be minimized. Consequently, a relatively small actuation displacement causes a relatively large displacement of the guide 122 and, therefore, the grasping arms 124a, 124b also.

The contemporaneous motion of tube 130 and guide 122 relative to each other causes tube 130 to advance around grasping arms 124a, 124b and close the grasping arms 124a, 124b around the tissue. By continuing to actuate levers 110a, 110b, a user may grasp and hold the tissue (e.g., extract it from the eye).

System 100 may have a variety of uses during ocular surgery. For example, it may be used for grasping and/or cutting tissues. Moreover, it may be used in the anterior or posterior parts of the eye.

System 100 has a variety of features. For example, by providing a curved tube 130 with a curved guide 122 disposed therein, system 100 may provide improved accessibility for a physician, especially in comparison to a straight arm. Consequently, a relatively small actuation displacement causes a comparatively larger displacement of guide 122 (i.e., tip displacement), and, therefore, actuation of the grasping members 124a. 124b results as a result of a small displacement of the levers 110a, 110b. The closing characteristics, e.g., an amount of actuation displacement, an amount of tip displacement, a rate of movement of the guide mechanism 160 for a given displacement of the levers 110a, 110b, and/or an amount of tip displacement for a given displacement of the levers 110a, 110b) may be defined by a geometrical configuration (e.g., orientation, angle, etc.) of the hinge members 142a, 142b and hinge members 144a, 144b. The concepts of system 100 may also be applied to a variety of curved vitreoretinal-type and cataract-type instruments.

Although FIG. 1 illustrates a system for ocular tissue manipulation, a variety of additions, deletions, substitutions, and modifications may be made to system 100 while still achieving ocular tissue manipulation. For example, tube 130 may have a shape other than a curved shape. For example, tube 130 may be straight. As another example, four hinge members may not be required. As a further example, member 170 may be omitted in some implementations. As an additional example, levers 110a, 110b may be coupled to other components that the user actually manipulates. Those components may, in turn, actuate levers 110a, 110b.

Although FIG. 2 illustrates one example of a guide mechanism, other guide mechanisms may include fewer, additional, and/or a different arrangement of components. For example, a guide mechanism may not include channel 104. As another example, a guide mechanism may not receive member 170. As a further example, a guide mechanism may not receive tube 130.

Figure 3A:
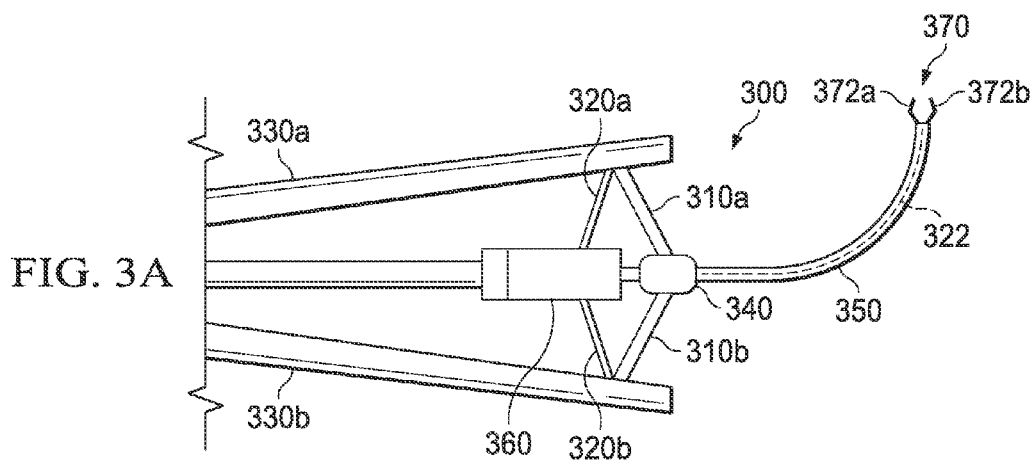
FIGS. 3A-B show an example hinge assembly for an ocular tissue manipulation system.
Figure 3B:
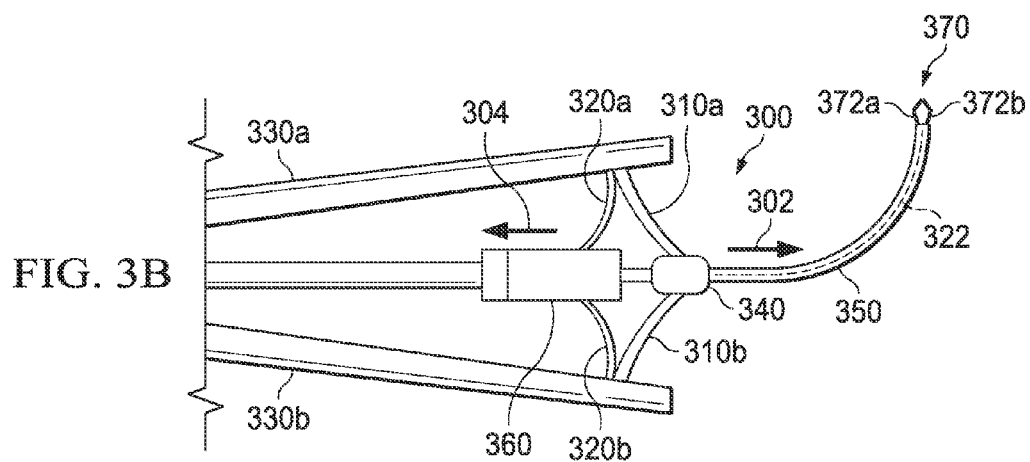

FIGS. 3A-B illustrate an example hinge assembly 300 for a system for manipulating ocular tissue. In particular, FIG. 3A shows hinge assembly 300 in a neutral position in which grasping arms 372a, 372b are extended, and FIG. 3B shows hinge assembly 300 in an actuated position in which grasping arms 372a, 372b are retracted. Hinge assembly 300 may, for example, be used with a system similar to system 100.

Hinge assembly 300 includes two front hinge members 310a, 310b and two rear hinge members 320a, 320b. Front hinge members 310a, 310b are respectively coupled to levers 330a, 330b, which may be manipulated by a user in a pinching-like motion. Front hinge members 310a, 310b may be integral with, fused to, pinned to, or otherwise coupled to levers 330a, 330b. Front hinge members 310a, 310b are also coupled to a hub 340, which is coupled to a curved tube 350. Hub 340 may be integral with, fused to, adhered to, or otherwise coupled to tube 350.

Rear hinge members 320a, 320b are also respectively coupled to levers 330a, 330b. Rear hinge members 320a, 320b may be integral with, fused to, pinned to, or otherwise coupled to levers 330a, 330b. Rear hinge members 320a, 320b are also coupled to a guide mechanism 360. Also coupled to guide mechanism 360 is a grasping mechanism 370, which, at least in part, passes through tube 350. For example, the grasping mechanism 370 may include grasping arms 372a, 372b and a guide 322 passing through the tube 350. In a manner similar to that described above, the guide 322 may be coupled to the guide mechanism 360. In certain implementations, guide mechanism 360 may also slideably receive tube 350.

FIG. 3A illustrates hinge assembly 300 at a point where levers 330a, 330b have not been manipulated. Thus, front hinge members 310a, 310b and rear hinge members 320a, 320b are relatively unstressed and straight. When a user presses levers 330a, 330b toward each other, front hinge members 310a 310b and rear hinge members 320a, 320b deform in a curved-like manner, as shown in FIG. 3B. As front hinge members 310a, 310b deform, they push hub 340 away from levers 330a, 330b in the direction of arrow 302. Hub 340, in turn, pushes tube 350 along grasping mechanism 370. As rear hinge members 320a, 320b deform, they push guide mechanism 360 further in the direction of arrow 304. Because guide mechanism 360 is coupled to grasping mechanism 370, the movement of the guide mechanism 360, in turn, pulls grasping mechanism 370 in the direction of arrow 304. Thus, hinge assembly 300 provides a contemporaneous relative movement between tube 350 and grasping mechanism 370, which may provide for retraction of the grasping arms 372a, 372b.

When a user releases levers 330a, 330b, the levers 330a, 330b may return to their original position. Thus, hinge members 310a, 310b, 320a, and 320b may resume their initial configuration.

Although FIGS. 3A-3B illustrate an example hinge assembly, other hinge assemblies may include fewer, additional, and/or a different arrangement of components. For example, one or more of the hinge members of a hinge assembly may not bend during actuation. For instance, one or more of the hinge members may only pivot relative to the parts connected thereby. Moreover, in certain implementations, one or more of the hinge members may be bent in their unstressed state and straighten when stressed. As another example, a hinge assembly may be used with a straight tube instead of a curved one. As an additional example, fewer or additional hinge members may be used.

Figure 4:
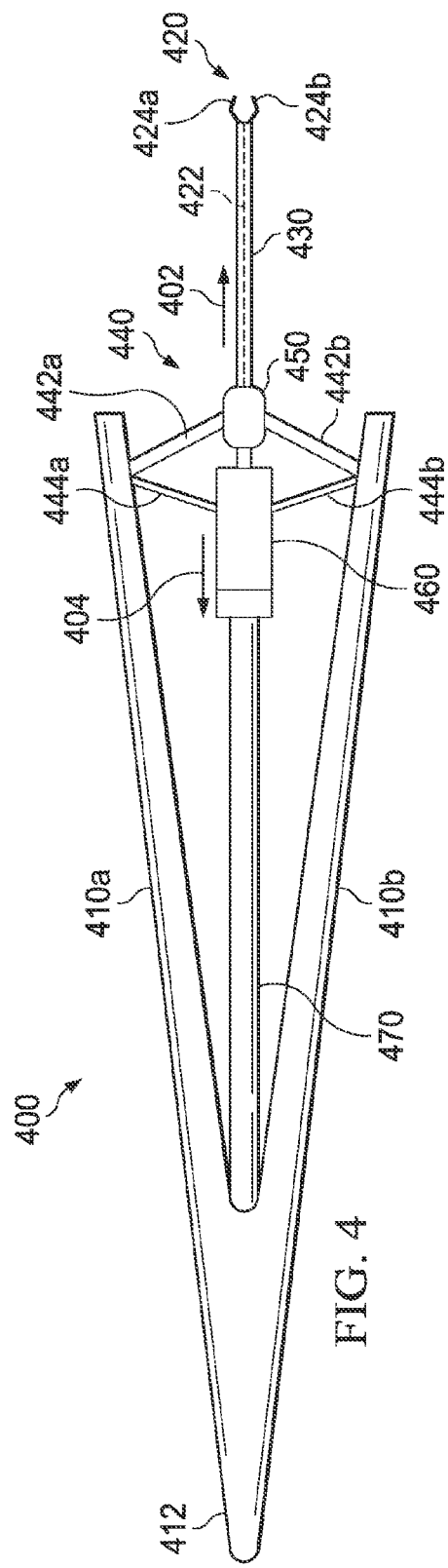
FIG. 4 shows a side view of another example system for tissue manipulation during ocular surgery.

FIG. 4 illustrates another example system 400 for tissue manipulation during ocular surgery. System 400 includes a pair of levers 410a, 410b, a grasping mechanism 420, and a tube 430. In operation, manipulation of levers 410a, 410b toward each other causes tube 430 to extend and activate grasping mechanism 420. System 400 may be sized for removing particles from an eye during ocular surgery (e.g., vitreoretinal surgery).

Levers 410a, 410b are generally elongated and are coupled to each other at an end 412 in a manner to allow movement of the levers toward each other (e.g., in a pinching-like manner). Levers 410a, 410b may, for example, be integral, pinned, fused, or otherwise coupled to each other at end 412. Levers 410a, 410b may be made of stainless steel, titanium, plastic, or any other appropriate material.

In the illustrated implementation, a user may manipulate levers 410a, 410b by grasping them between thumb and fingers and moving the levers 410a, 410b towards each other (e.g., in a pinching-like motion). In certain implementations, levers 410a, 410b may be part of a larger device, and the user may manipulate other portion of the device (e.g., handles) to manipulate levers 410a, 410b.

Grasping mechanism 420 includes a guide 422 that extends from a guide mechanism 460 disposed between levers 410a, 410b and two or more grasping arms 424a, 424b coupled to the distal end of guide 422. Guide 422 links grasping arms 424a, 424b to the actuation of levers 410a, 410b. Guide 422 may, for example, be a metal wire or a plastic filament, with round, oval, rectangular, or other appropriate cross-section. In particular implementations, guide 422 may be sufficiently rigid to maintain a linear shape during actuation of system 400. Grasping arms 424a, 424b may be coupled together at the distal end of guide 422 in a manner to allow movement of the grasping arms 424a, 424b relative to each other. Particularly, the grasping arms 424a. 424b may be operable to pivot towards each other (e.g., in a pinching-like manner) in response to engagement by tube 430. Further, the grasping arms 424a, 424b may include a bias such that, when engagement by the tube 430 is removed, the grasping arms 424a, 424b return to their initial, open configuration. Grasping arms 424a, 424b may, for example, be pinned or fused at the distal end of guide 422. In other implementations, the guide 422 and grasping members 424a, 424b may be integrally formed. For example, the guide 422 and grasping members 424a, 424b may be formed from a single piece of metal. Alternately, the guide 422 and grasping member 424a, 424b may be integrally formed via an injection molding process, e.g., plastic injection molding. Grasping mechanism 420 may be made of stainless steel, titanium, plastic, or any other appropriate material.

At least a portion of the guide 422 may extend through tube 430 and be coupled to the guide mechanism 460. The grasping arms 424a, 424b may extend distally from the distal end of tube 430. Tube 430 may have a circular, oval, rectangular, or other cross-section and be made of metal, plastic, or any other appropriate material. In certain implementations, tube 430 may have sufficient rigidity to maintain the straight shape during actuation of system 400.

System 400 also includes a hinge assembly 440, a hub 450, and a member 470. These components cooperate with each other to extend tube 430 over guide 422 of grasping mechanism 420 when levers 410a, 410b are manipulated.

In the illustrated implementation, hinge assembly 440 includes two front hinge members 442a, 442b and two rear hinge members 444a, 444b. Front hinge members 442a, 442b extend between and are coupled to levers 410a, 410b and hub 450. The hub 450 is coupled to tube 430. Front hinge members 442a, 442b may be coupled to levers 410a, 410b and/or hub 450 by being integral to, pinned to, fused to, or otherwise coupled to the components. In some implementations, the coupling may allow rotation of the front hinge members 442a, 442b at the coupling location, and in some implementations, the coupling may not allow rotation at the coupling location. Hub 450 may be integral with, fused to, adhered to, or otherwise coupled to tube 430.

Rear hinge members 444a, 444b extend between and are respectively coupled to levers 410a, 410b and to guide mechanism 460. Rear hinge members 444a, 444b may be coupled to levers 410a, 410b and/or guide mechanism 460 by being integral to, pinned to, fused to, or otherwise coupled to the components. In some implementations, the coupling may allow rotation of the rear hinge members 444a, 444b at the coupling location, and in some implementations, the coupling may not allow rotation at the coupling location. Guide mechanism 460 receives guide 422 of grasping mechanism 420 and member 470, which extends between levers 410. For example, the guide mechanism 460 may receive guide 422 and member 470 in a manner similar to that described above. Particularly, in some implementations, the guide mechanism 460 may receive guide 422 and member 470 in a manner similar to that described with respect to FIG. 2. However, the configuration of these components may be arranged in any way described herein or otherwise within the scope of the disclosure. Guide 422 is coupled to guide mechanism 460 so that the guide 422 moves axially therewith. Guide mechanism 460 slideably receives member 470 so that guide mechanism 460 is guided axially along member 470.

In certain modes of operation, system 400 is operated by a user grasping levers 410a, 410b and positioning grasping arms 424a, 424b in proximity (e.g., around) to a tissue to be grasped. Once the grasping arms 424a, 424b are in proximity to the tissue to be grasped, the user manipulates levers 410a, 410b toward each other. The motion of levers 410a, 410b toward each other causes front hinge members 442a, 442b to move (e.g., by swinging, bending, or otherwise) in the direction of arrow 402. The movement of front hinge members 442a, 442b also causes hub 450 to move in the direction of arrow 402. Because hub 450 is coupled to tube 430, the movement of hub 450 also causes tube 430 to move in the direction of arrow 402.

At about the same time that front hinge members 442a, 442b are moving in the direction of arrow 402, rear hinge members 444a, 444b are moving in the direction of arrow 404. The movement of rear hinge members 444a, 444b causes guide mechanism 460 to move in the direction of arrow 404. Because guide 422 is coupled to guide mechanism 460, movement of guide mechanism 460 in the direction of arrow 404 causes guide 422 also to move in the direction of arrow 404. Moreover, because guide mechanism 460 slideably receives member 470, guide mechanism 460 moves along member 470 in the direction of arrow 404.

The contemporaneous motion of tube 430 and guide 422 relative to each other causes tube 430 to engage grasping arms 424a, 424b, thereby causing the grasping arms 424a. 424b to close or retract around the tissue. By continuing to close levers 410a, 410b, a user may hold the tissue between the grasping arms 424a, 424b. The tissue may then be subject to other activities, such as extraction from the eye.

System 400 may have a variety of uses during ocular surgery. For example, it may be used for grasping and/or cutting tissues. Moreover, it may be used in the anterior or posterior parts of the eye.

System 400 has a variety of features. For example, because guide 422 moves proximally at about the same time that tube 430 moves distally, an amount of movement of the grasping arms 424a, 424b in the proximal direction necessary to fully close the grasping arms 424a. 424b is reduced.

The concepts of system 400 may also be applied to a variety of straight vitreoretinal-type instruments.

FIG. 5 shows another example instrument 500. Instrument 500 may be similar in some ways to the example instruments 100, 300, and 400 in all ways other than the configuration of hinge members 544a, 544b. In contrast to the instruments 100, 300, and 400, the hinge members 544a, 544b are oriented in manner similar to hinge members 142a, 142b. That is, the connection location of the hinge members 544a, 544b at the levers 110a, 110b is proximal of the connection location of the hinge members 544a, 544b at a guide mechanism 160. In some instances, an angle A at which the hinge members 544a, 544b extend from respective levers 110a, 110b may be different from the angle B at which hinge members 142a, 142b extend from the levers 110a, 110b. In some instances, the angle A may be greater than angle B. In other instances, angle A may be smaller than angle B. In still other instances, angle A may be the same as angle B.

Generally, a user grasps instrument 500 with fingers. For example, a user may grasp instrument 500 with an index finger and thumb. In the example shown, a user's fingers may contact the levers 110a, 110b at locations 550a, 550b, respectively. However, a user may grasp the instrument 500 at any desired location(s). The locations 550a, 550b are provided merely as an example.

During actuation of instrument 500, locations 550a and 550b move along an arc due to pivoting of the levers 110a and 110b about end 112. The locations 550a and 550b move slightly axially in the direction of arrow 131 as a result of this arc-shaped travel. In order to maintain a constant or substantially constant axial distance between the locations 550a, 550b and the grasping member 124a, 124b, the hinge members 544a, 544b are configured such that actuation of the levers 110a, 110b causes the guide mechanism 160 and the guide 122 coupled thereto to move in the direction of arrow 131. Thus, a component of the movement of the locations 550a, 550b and the grasping members 124a, 124b are in the same direction, i.e., in the direction of arrow 131. The amount of axial displacement of the grasping members 124a, 124b may be adjusted by alteration of angle A of the hinge members 544a, 544b. As a result, the grasping members 124a, 124b may be made to maintain a constant axial distance relative to the locations 550a, 550b. This provides improved control and performance during a surgical procedure.

In operation, manipulation of levers 110a, 110b toward each other also causes tube 130 to move in the direction of arrow 131. Thus, the grasping members 124a, 124b and the tube 130 move in the direction of arrow 131. The configuration of the hinge members 544a, 544b and hinge members 142a, 142b may be established (e.g., by selection of respective angles A and B) such that the rate at which the grasping mechanism 120 moves in the direction of arrow 131 may be less than the rate at which tube 130 moves in the direction of arrow 131. This distal movement of the guide 122 and, correspondingly, grasping arms 124a, 124b, in the direction of arrow 131 reduces or substantially eliminates this movement relative to a fixed point in space.

Further, the relative angles A and B can be altered to cause the guide 122 and the tube 130 to move at different rate relative to each other. Consequently, the angles A and B may be selected such that the tube 130 moves at a faster rate relative to the movement of guide 122 during actuation of the instrument 500 such that the tube 130 engages the grasping members 124a, 124b, causing them to close.

The example instrument 500 shown in FIG. 5 includes a straight tube 130. However, in other implementations, the instrument 500 may include a curved tube, similar, for example, to tube 130 shown in FIGS. 1, 3A, and 3B. Moreover, the shape of the tube may be any desired shape and the examples provided herein are not intended to be limiting.

Further, the guide in any of the examples described herein and as encompassed by this disclosure, such as guide 122, may have a shape corresponding to or otherwise compatible with the shape of the tube, such as tube 130. For example the guide 122 may be formed from a flexible material that conforms to the shape of the tube 130. Particularly, the guide 122 may be formed of a material that has sufficient compliance to conform to the shape of the tube 130 throughout the entire range of actuation of the instrument, such as instrument 100, 300, 400, or 500.

Although FIGS. 4 and 5 illustrate systems for ocular tissue manipulation, a variety of additions, deletions, substitutions, and modifications may be made to systems 400 and 500 while still achieving ocular tissue manipulation. For example, a system may include additional or fewer hinge members. As a further example, another example system may not include a member similar to member 470 or 170. As an additional example, levers may be coupled to other components that the user actually manipulates, and those components may actuate the levers.

The various implementations discussed and mentioned herein have been used for illustrative purposes only. The implementations were chosen and described in order to explain the principles of the disclosure and the practical application and to allow those of skill in the art to understand the disclosure for various implementations with various modifications as are suited to the particular use contemplated. Thus, the actual physical configuration of components may vary. For example, the mentioned size(s) of components and their illustrated sizing relative to each other may vary based on application. Moreover, the shapes of one or more components may vary depending on application. Thus, the illustrative implementations should not be construed as defining the only physical size, shape, and relationship of components.

Various systems and techniques for tissue manipulation during ocular surgery have been discussed, and several others have been mentioned or suggested. However, those skilled in the art will readily recognize that a variety of additions, deletions, substitutions, and modifications may be made to these systems and techniques while still achieving tissue manipulation during ocular surgery. Thus, the scope of protection should be judged based on the following claims, which may capture one or more aspects of one or more implementations.

The invention claimed is:

1. A system for tissue manipulation during ocular surgery, the system comprising:
   at least two spaced apart levers, the levers coupled together at one end;
   a first hinge member extending from one of the levers to a guide mechanism located between the levers, the first hinge member adapted to displace the guide mechanism in one of a proximal or distal direction when the levers are moved toward each other;
   a grasping mechanism coupled at a proximal end to the guide mechanism, the grasping mechanism extending distally from the guide mechanism;
   a second hinge member extending from one of the levers and coupled to a tube that surrounds a portion of the grasping mechanism, the second hinge member adapted to displace the tube distally when the levers are moved towards each other such that the tube moves relative to the guide mechanism; and a third hinge member extending to the guide mechanism from the lever opposite the lever from which the first hinge member extends, the third hinge member also adapted to move the guide mechanism in one of a proximal or distal direction when the levers are moved toward each other; and a fourth hinge member coupled to the tube and extending from the lever opposite the lever from which the second hinge member extends, the fourth hinge member adapted to move the tube distally when the levers are moved toward each other, wherein movement of the guide mechanism relative to the tube causes the tube to engage the grasping mechanism such that the grasping mechanism is actuated.

2. The system of claim 1, wherein at least one of the hinge members is adapted to bend when the levers are moved towards each other.

3. The system of claim 2, wherein at least one of the hinges is adapted to form a curved shape when bent.

4. The system of claim 1, further comprising a member extending between the levers and slideably receivable into the guide mechanism.

5. The system of claim 1, wherein the tube is slideably receivable into the guide mechanism.

6. The system of claim 1, wherein the second hinge member is coupled to a hub that surrounds the tube, the hub being coupled to the tube.

7. The system of claim 1, wherein the grasping mechanism comprises:
a guide that extends through a passage formed in the tube; and
actuatable grasping arms disposed at a distal end of the guide.

8. The system of claim 7, wherein the grasping arms are moveable towards each other when engaged by a distal end of the tube.

9. The system of claim 1, wherein the tube is curved.

10. A system for tissue manipulation during ocular surgery, the system comprising:
at least two spaced apart levers, the levers coupled together at one end;
a first hinge member extending from one of the levers to a guide mechanism located between the levers, the first hinge member adapted to displace the guide mechanism in one of a proximal or distal direction when the levers are moved toward each other;
a grasping mechanism coupled at a proximal end to the guide mechanism, the grasping mechanism extending distally from the guide mechanism; and
a second hinge member extending from one of the levers and coupled to a tube that surrounds a portion of the grasping mechanism, the second hinge member adapted to displace the tube distally when the levers are moved towards each other such that the tube moves relative to the guide mechanism,
wherein movement of the guide mechanism relative to the tube causes the tube to engage the grasping mechanism such that the grasping mechanism is actuated,
wherein the tube is slideably receivable into the guide mechanism.

11. The system of claim 10, further comprising:
a third hinge member extending to the guide mechanism from the lever opposite the lever from which the first hinge member extends, the third hinge member also adapted to move the guide mechanism in one of a proximal or distal direction when the levers are moved toward each other; and
a fourth hinge member coupled to the tube and extending from the lever opposite the lever from which the second hinge member extends, the fourth hinge member adapted to move the tube distally when the levers are moved toward each other.

12. The system of claim 10, wherein at least one of the hinge members is adapted to bend when the levers are moved towards each other.

13. The system of claim 12, wherein at least one of the hinges is adapted to form a curved shape when bent.

14. The system of claim 10, further comprising a member extending between the levers and slideably receivable into the guide mechanism.

15. The system of claim 10, wherein the second hinge member is coupled to a hub that surrounds the tube, the hub being coupled to the tube.

16. The system of claim 10, wherein the grasping mechanism comprises:
a guide that extends through a passage formed in the tube; and
actuatable grasping arms disposed at a distal end of the guide.

17. The system of claim 16, wherein the grasping arms are moveable towards each other when engaged by a distal end of the tube.

18. The system of claim 10, wherein the tube is curved.

* * * * *